(12) United States Patent
Wang et al.

(10) Patent No.: US 9,823,244 B1
(45) Date of Patent: Nov. 21, 2017

(54) DIGITAL PROGRESSIVE COMPRESSION DRIVEN FLOW CARTRIDGE FOR ANALYTE DETECTING DEVICE AND METHOD

(71) Applicant: DNT SCIENTIFIC RESEARCH, LLC, San Diego, CA (US)

(72) Inventors: Naishu Wang, Poway, CA (US); Michael Chang Chien, Cerritos, CA (US); Jiwei Ying, Poway, CA (US)

(73) Assignee: DNT SCIENTIFIC RESEARCH, LLC, San Diego, CA (US)

( * ) Notice: Subject to any disclaimer, the term of this patent is extended or adjusted under 35 U.S.C. 154(b) by 0 days.

(21) Appl. No.: 15/664,199

(22) Filed: Jul. 31, 2017

(51) Int. Cl.
G01N 31/22 (2006.01)
G01N 33/543 (2006.01)
G01N 33/558 (2006.01)

(52) U.S. Cl.
CPC ..... G01N 33/54386 (2013.01); G01N 33/558 (2013.01)

(58) Field of Classification Search
CPC ................. G01N 33/54386; G01N 33/558
See application file for complete search history.

(56) References Cited

U.S. PATENT DOCUMENTS

| | | | |
|---|---|---|---|
| 4,299,916 A | 11/1981 | Litman et al. | |
| 4,366,241 A | 12/1982 | Tom et al. | |
| 5,352,410 A | 10/1994 | Hansen et al. | |
| 5,403,551 A | 4/1995 | Galloway et al. | |
| 5,656,503 A | 8/1997 | May et al. | |
| 6,140,136 A | 10/2000 | Lee | |
| 6,372,514 B1 | 4/2002 | Lee | |
| 6,379,620 B1 | 4/2002 | Tydings et al. | |
| 6,403,383 B1 | 6/2002 | Casterlin et al. | |
| 6,730,268 B2 | 5/2004 | Lee et al. | |
| 6,805,837 B2 | 10/2004 | Tydings | |
| 6,875,185 B2 | 4/2005 | Wong et al. | |
| 7,431,882 B2 | 10/2008 | Parker | |
| 7,741,103 B2 | 6/2010 | Guirguis | |
| D626,249 S | 10/2010 | Wang et al. | |
| 7,879,623 B2 | 2/2011 | Guirguis | |

(Continued)

OTHER PUBLICATIONS

Office Action dated Aug. 10, 2017 from related U.S. Appl. No. 15/630,174.

(Continued)

*Primary Examiner* — Dennis White
(74) *Attorney, Agent, or Firm* — Innovation Capital Law Group, LLP; Vic Lin

(57) ABSTRACT

A progressive compression test cartridge that is adapted with driven flow technology that can be coupled with a digital electronic device to make the test reading result more reliable quantitatively than visual interpretation. The test cartridge can provide test results typically in one minute or less. The test cartridge can accept a sample via a droplet or a stream sampling method. In the stream sampling method, the open end of the test cartridge allows the sample pad of the test strip to be exposed to the stream of fluid. A refracting pad on the base of the test cartridge can refract the original stream vector partially along the sample pad then continue flowing to elute and release the nanoparticles from the conjugate pad onto the membrane which is pre-coated with reactant(s). Collimated compression bars can prevent flooding sample by restricting the top and bottom surface of the conjugated pad.

20 Claims, 12 Drawing Sheets

(56) References Cited

U.S. PATENT DOCUMENTS

| | | |
|---|---|---|
| 7,981,382 B2 | 7/2011 | Wong et al. |
| 8,021,625 B2 | 9/2011 | Wang et al. |
| 8,163,253 B1 | 4/2012 | Hartselle |
| 8,206,661 B2 | 6/2012 | Vallejo et al. |
| 8,394,626 B2 | 3/2013 | Ramsey et al. |
| 8,889,424 B2 | 11/2014 | Ehrenkranz et al. |
| 8,916,390 B2 | 12/2014 | Ozcan et al. |
| 8,940,527 B2 | 1/2015 | Guirguis |
| 8,992,855 B2 | 3/2015 | Lin |
| 9,377,457 B1 | 6/2016 | Wang et al. |
| 9,414,813 B2 | 8/2016 | Engel et al. |
| 9,535,061 B1 | 1/2017 | Wang et al. |
| 2004/0152206 A1 | 8/2004 | Davis et al. |
| 2005/0163660 A1 | 7/2005 | Wang |
| 2006/0292700 A1 | 12/2006 | Wang et al. |
| 2007/0065339 A1 | 3/2007 | Huff |
| 2007/0259442 A1 | 11/2007 | Gould et al. |
| 2008/0199851 A1 | 8/2008 | Egan et al. |
| 2009/0208371 A1 | 8/2009 | Hannant et al. |
| 2010/0278692 A1 | 11/2010 | Chen |
| 2013/0022517 A1 | 1/2013 | Engel et al. |
| 2015/0173742 A1 | 6/2015 | Palese et al. |
| 2015/0203904 A1 | 7/2015 | Hopper |
| 2015/0211987 A1 | 7/2015 | Burg et al. |
| 2016/0025752 A1 | 1/2016 | Santiago et al. |

OTHER PUBLICATIONS

Office Action dated Aug. 25, 2017 from related U.S. Appl. No. 15/620,216.

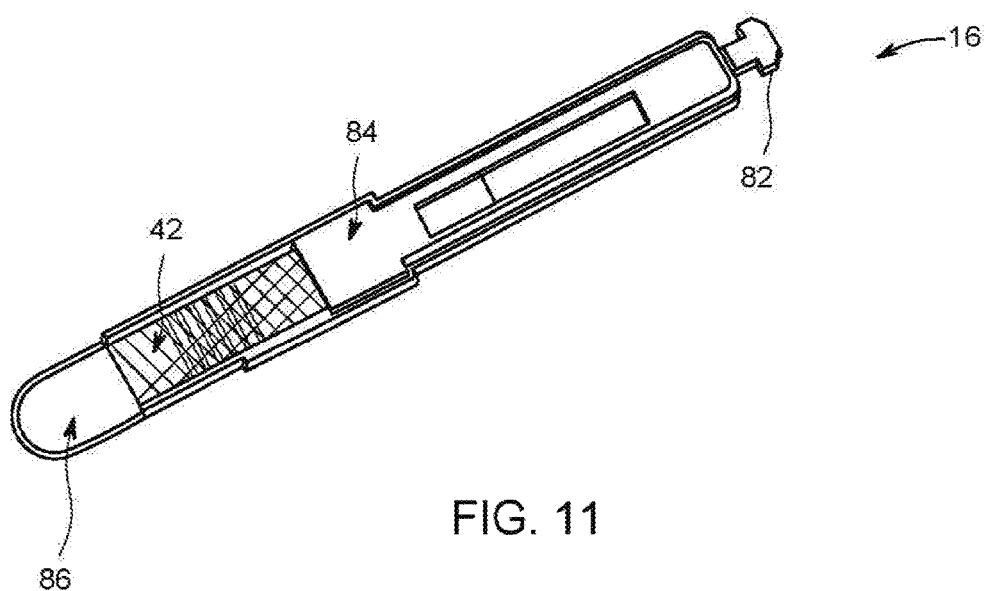
FIG. 11
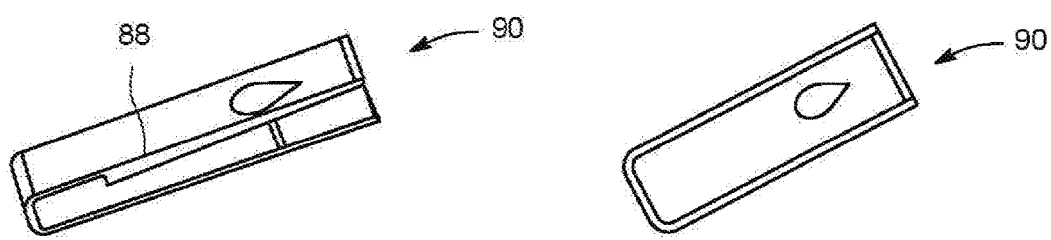
FIG. 12A
FIG. 12B

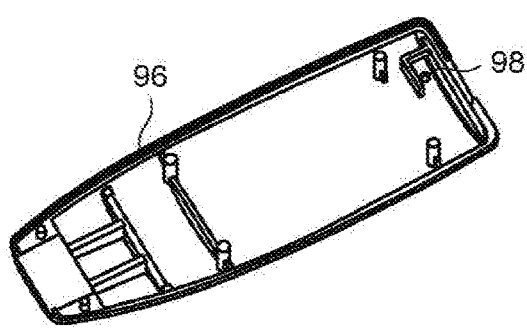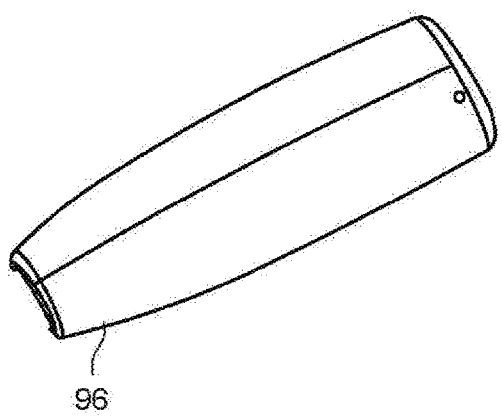
FIG. 15A  FIG. 15B
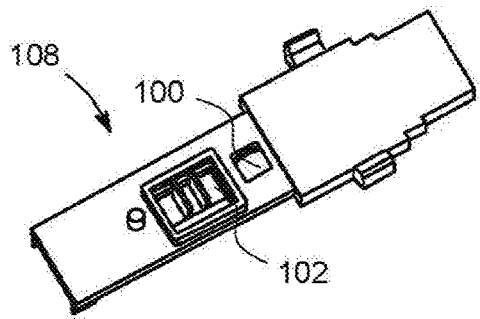
FIG. 16
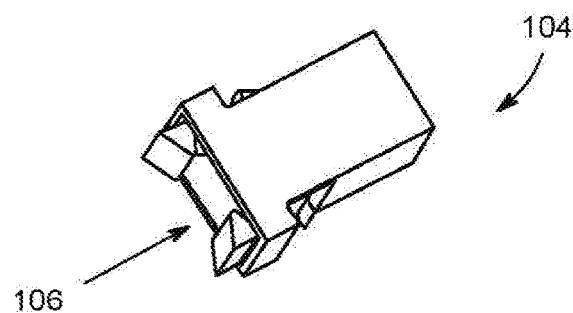
FIG. 17

DIGITAL PROGRESSIVE COMPRESSION DRIVEN FLOW CARTRIDGE FOR ANALYTE DETECTING DEVICE AND METHOD

BACKGROUND OF THE INVENTION

1. Field of the Invention

One or more embodiments of the invention relate generally to apparatus for analyzing liquids, such as body fluids, using labeled molecular affinity binding, such as immunochromatography. The present invention further relates to an electronic device for reading the analysis apparatus. More particularly, the invention relates to test strip apparatus for detecting an analyte, such as an antibody or antigen, which may indicate a particular condition, as well as a digital electronic device for reading results from the test strip apparatus.

2. Description of Prior Art and Related Information

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Labeled molecular affinity binding such as immunochromatographic assays have existed for decades and have proven to be an inexpensive way to screen for various conditions such as abused drugs and other conditions such as pregnancy, cancer, or for single or multiple pathogenic conditions such as HIV infection.

In the point-of-care test (POCT) setting, immunochromatographic assays are typical conducted using lateral flow strip technology as described in May et al., U.S. Pat. No. 5,656,503 incorporated herein by reference. Unfortunately, although they can be fast, inexpensive, and simple-to-use, depending on the type of condition being detected, these tests provide a typical accuracy of between 75% and 95%, falling short of the 99% or above accuracy generally considered to be necessary for a confirmatory test, and providing no objective measure of a quantitative result, i.e. the concentration of a given drug present in the liquid being tested.

The reasons for the insufficient accuracy in many rapid IVD test devices are primarily due to their current lack of overall higher sensitivity and specificity. Different samples may contain chemicals or particles which intrinsically inhibit the rapid and well mixed liquid flow or otherwise interfere with one or both of the first and second affinity binding reactions.

Prior devices have attempted to enhance sensitivity or specificity by pretreating various parts of the device with reaction or flow enhancing reagents, pH conditioning chemicals, or even non-specific adhesive blocking molecules which will "block-out" non-analyte molecules which might cause non-specific adhesion, or otherwise compete with the analyte in question for specific binding members, especially in the reaction zones region of the strip. These attempts have met with limited success in some types of testing, but do not provide the desired accuracy in many others. Also, pretreatment with two or more of the above pretreatments exacerbates the difficulties in obtaining uniform manufacturing due to potential incompatibilities between the pretreatment chemicals. For example, the pH conditioner might disrupt the effectiveness of the non-specific blocking member molecules. Or, the manufacturing step of pretreating with the second pretreatment chemical can dislodge some of the first pretreatment chemical.

Further, lot-to-lot variation in the manufacture of many IVD test devices can often lead to ambiguous results, such as false negatives as well as weak false positives, so-called "ghost lines" or "phantom lines". False negatives typically occur when non-specific molecules interfere with the first and/or second affinity binding actions. It has been found that non-analyte molecules can clump together in liquid samples that are not well mixed so that they temporarily prevent access between analytes and binding members. Even temporary interference in past devices can prevent an adequate number of labeled analyte complexes and/or ultimately immuno-sandwich complexes from forming. In this way, if a non-analyte molecule or clump of molecules blocks access between analytes and binding members for only a few seconds, it may be enough to induce a false negative result. Further, clumps of non-analyte molecules can carry an overabundance of the labeled mobilizable binding members to the second affinity binding site to generate a false positive result.

One area of recent improvement in rapid diagnostic testing involves using the capabilities offered by mobile communication devices such as smart phones. As disclosed in Ozcan et al., U.S. Pat. No. 8,916,390, incorporated herein by reference, a lateral flow-type strip can be automatedly scanned by the camera of a smart phone which can be interpreted by software to obtain a result and deliver it to a wireless network. Lateral flow devices are useful due to their low cost and ease of use. However, prior lateral flow devices suffer from low accuracy as detailed above. This is especially true for saliva testing because of the low concentrations of analytes present. Current lateral flow strips cannot provide the necessary sensitivity and specificity within the time normally allotted to a typical law enforcement action such as a traffic stop.

The low accuracy can be due to a number of problems unique to lateral flow-type tests. First, there is often uneven movement of the immunoparticles within the nitrocellulose membrane. Smaller, non-analyte molecules mixed together with the larger analyte molecules and compete for sites and often prevent the larger molecules from reacting in the desired fashion.

Moreover, sometimes a testing result can fail because users are color blind and cannot read the color of the test and control lines on the test strip correctly.

Therefore, there is a need to improve the accuracy of rapid IVD test devices and methods for reading such test devices so that rapid inexpensive easily conducted quantitative immunological testing becomes a reality.

SUMMARY OF THE INVENTION

Embodiments of the present invention further provide a device for testing a liquid sample for the concentration of at least one analyte, comprising a test cartridge comprising a base component supporting a test strip, a top component fitting onto the base component, sandwiching the test strip with the base component, a plurality of compression bars on the top component, the compression bars aligning with a conjugate pad of the test strip when the test strip is positioned in the test cartridge, a refracting pad formed from an end of the base component, the refracting pad supporting a sample pad of the test strip when the test strip is positioned in the test cartridge, wherein the top component terminates prior to the refracting pad, permitting a fluid stream to be received on the sample pad, a sampling well on the top component providing another method for introducing dropped fluid, and a reservoir formed in the base component under the sample pad, the reservoir configured to contain excess fluid from the fluid stream directed at the sample pad.

Embodiments of the present invention provide a system for testing a liquid sample for the concentration of at least one analyte, comprising a test strip comprising a sample pad for receiving a sample, a conjugate pad containing nanoparticle conjugate, a test line for indicating a test result, and a control line for indicating the test result; a test cartridge comprising a base component supporting the test strip, a top component fitting onto the base component, sandwiching the test strip with the base component, a plurality of compression bars on the top component, the compression bars aligning with the conjugate pad of the test strip, a refracting pad formed from a first end of the base component, the refracting pad supporting the sample pad of the test strip, wherein the top component terminates prior to the refracting pad, permitting a fluid stream to be received on the sample pad, a sampling well on the top component providing another method of introducing a dropped fluid, a trigger head disposed on a second opposite end of the base component, and a reservoir formed in the base component under the sample pad, the reservoir configured to contain excess fluid from the fluid stream directed at the sample pad; and an electronic reading device, the electronic reading device comprising first and second light emitting diodes configured to deliver light to a test line and a control line of the test strip when the test cartridge is inserted into the electronic reading device, first and second photosensitive sensors for receiving a reflected light from each of the test line and the control line of the test strip, a microprocessor for receiving a signal from the first and second photosensitive sensors, and a trigger head receiver, receiving a trigger head of the test cartridge to activate reading of the test cartridge.

Embodiments of the present invention also provide a system for testing a liquid sample for the concentration of at least one analyte, comprising a test strip comprising a sample pad for receiving a sample, a conjugate pad containing nanoparticle conjugate, a test line for indicating a test result, and a control line for indicating the test result; a test cartridge comprising a base component supporting the test strip, a top component fitting onto the base component, sandwiching the test strip with the base component, a plurality of compression bars on the top component, the compression bars aligning with the conjugate pad of the test strip, a cushion on the bottom component, the cushion aligning with the plurality of compression bars to sandwich the conjugate pad of the test strip there between, and a reservoir formed in the base component under the sample pad, the reservoir configured to contain excess fluid from the fluid stream directed at the sample pad; and an electronic reading device, the electronic reading device comprising first and second light emitting diodes configured to deliver light to a test line and a control line of the test strip when the test cartridge is inserted into the electronic reading device, first and second photosensitive sensors for receiving a reflected light from each of the test line and the control line of the test strip, a microprocessor for receiving a signal from the first and second photosensitive sensors, and a shunt regulator for providing a constant power supply from a rechargeable battery.

These and other features, aspects and advantages of the present invention will become better understood with reference to the following drawings, description and claims.

BRIEF DESCRIPTION OF THE DRAWINGS

Some embodiments of the present invention are illustrated as an example and are not limited by the figures of the accompanying drawings, in which like references may indicate similar elements.

FIG. 11 is a plan view of the base component of the test cartridge of FIG. 1;

FIG. 12A is a cross-sectional view of a cap fitting on the test cartridge of FIG. 1;

FIG. 12B is a top view of the cap fitting on the test cartridge of FIG. 1;

FIG. 15A is a top view of a top housing of the electronic reading device;

FIG. 15B is a bottom view of the top housing of the electronic reading device;

FIG. 16 is a top view of a light mask used in the electronic reading device;

FIG. 17 is a perspective view of a trigger head receiver used in the electronic reading device;

Figure 1:
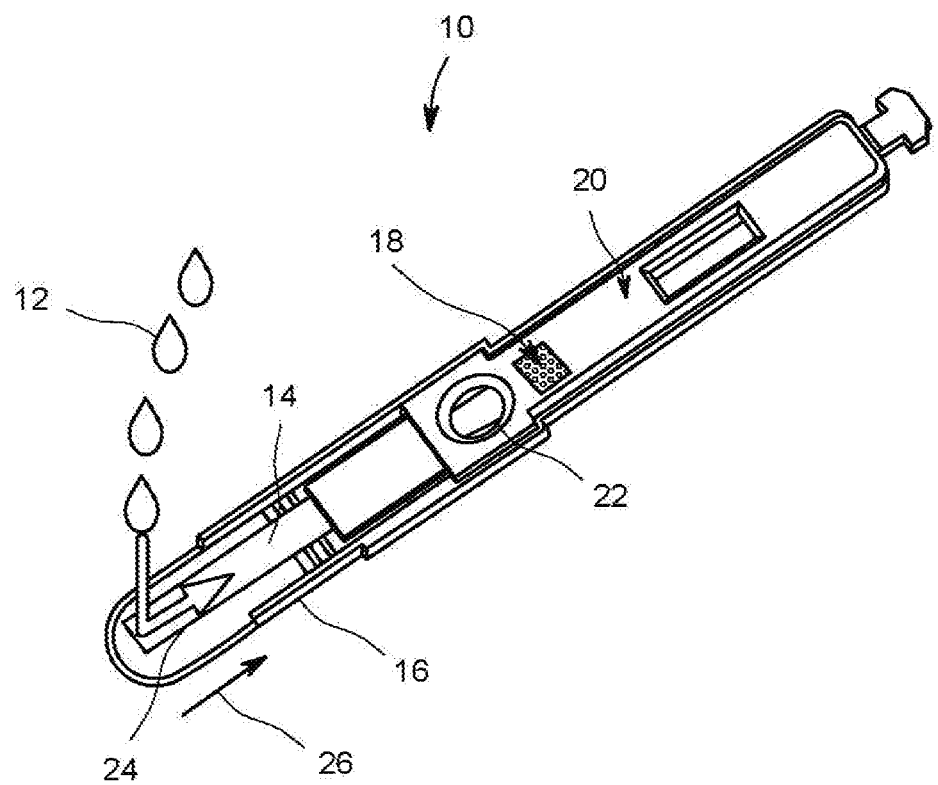
FIG. 1 is a perspective view of a driven flow test cartridge according to an exemplary embodiment of the present invention.

Unless otherwise indicated illustrations in the figures are not necessarily drawn to scale.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention, and is not intended to limit the invention to the specific embodiments illustrated by the figures or description below.

As is well known to those skilled in the art, many careful considerations and compromises typically must be made when designing for the optimal configuration of a commercial implementation of any system, and in particular, the embodiments of the present invention. A commercial implementation in accordance with the spirit and teachings of the present invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

Broadly, embodiments of the present invention provide a progressive compression test cartridge that is adapted with driven flow technology that can be coupled with a digital electronic device to make the test reading result more reliable quantitatively than visual interpretation. The test cartridge can provide test results typically in one minute or less. The test cartridge can accept a sample via a pipette or a stream sampling method. In the stream sampling method, the open end of the test cartridge allows the sample pad of the test strip to be exposed to the stream of fluid. A refracting pad on the base of the test cartridge can refract the original stream vector partially along the sample pad then continue flowing to elute and release the nanoparticles from the conjugate pad onto the membrane which is pre-coated with reactant(s). Collimated compression bars can stop flooding sample by restricting the top and bottom surface of the conjugated pad, where most of the flooding sample can be retained on the reservoir located before the conjugate pad.

Figure 2:
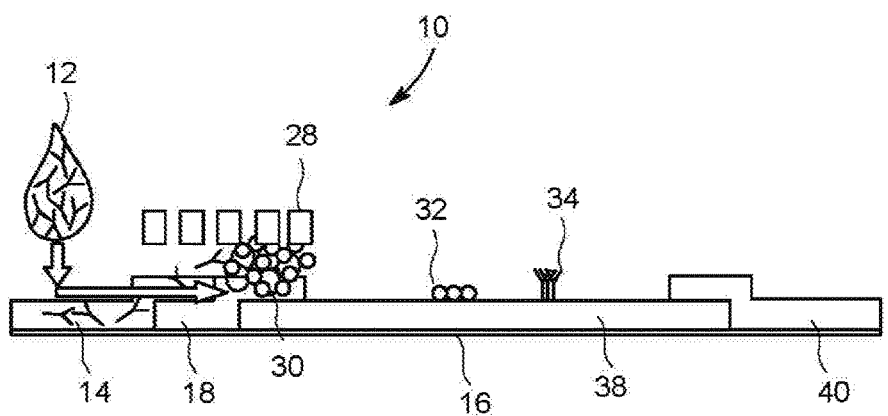
FIG. 2 is a side cross-sectional view of a test strip used in the test cartridge of FIG. 1.
Figure 3:
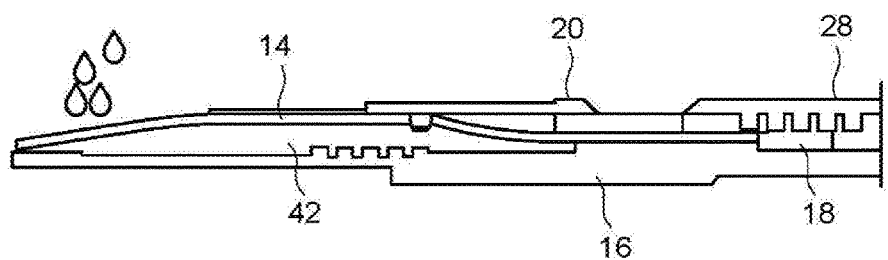
FIG. 3 is a side view of the test cartridge of FIG. 1, illustrating an excessive specimen reservoir, according to an exemplary embodiment of the present invention.

Referring to FIGS. 1 through 3, a sample stream 12 may be received onto a sample pad 14 of a test strip 24 positioned in a test cartridge 10. In some embodiments, a sample may be delivered by pipette, or some other fluid transfer device, to the sample well 22, formed as a hole in the top component 20 of the test cartridge 10. When the sample is from the sample stream 12, a portion of a base component 16 of the cartridge 10 may act as a refracting pad 86 (see FIG. 11) to refract the sample stream 12 vector partially along the sample pad as shown by arrow 26.

FIG. 2 shows a detailed view of the test strip with a portion of the top component 20 removed. The test strip can include the sample pad 14 that can deliver sample to a conjugate pad 18 containing nanoparticles conjugate 30 therein. Compression bars 28 of the top component 20 can create a limited flow channel through which sample may pass along the test strip. The sample and nanoparticles conjugate 30 may pass onto the nitrocellulose membrane 38 of the test strip and interact with a test line 32 and a control line 34. The test line 32 and control line 34 may be read by eye or by an electronic reading device 62 (see FIG. 5), as described in greater detail below. An absorbent pad 40 may be disposed on a distal end of the test strip.

As shown in FIG. 3, the sample pad 14 may be disposed over a reservoir 42 formed on the base component 16. During running tests by the stream method, most concern to cause test failure is so called "flooding" which applies excessive amounts of sample through the conjugate pad 18. In the present invention, the collimated compression bars 28 stop the flooding sample by restricting the top and bottom surface of the conjugate pad 18, thus most of the flooding sample will be retained on the reservoir 42 located before the conjugate pad 18. Thus, the conjugate pad 18 is sandwiched at an appropriate pressure between the compression bars 28 and the surface of the base 16. Such an appropriate pressure helps releasing specific labeled molecules, such as the nanoparticle conjugate 30 under the stream force.

Figure 4:
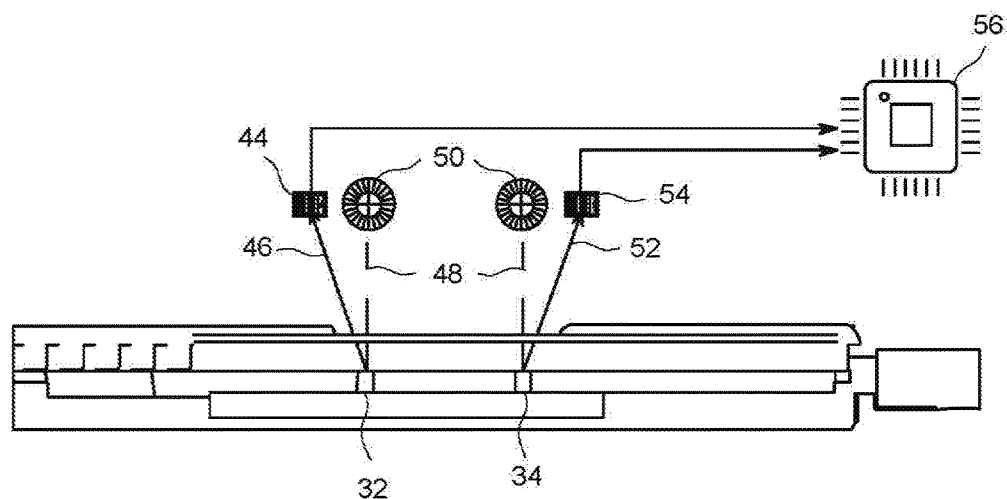
FIG. 4 is a detailed side cross-sectional view of the test cartridge of FIG. 1, illustrating photosensitive sensors used to detect light reflecting from the test line and the control line of the test strip.
Figure 5:
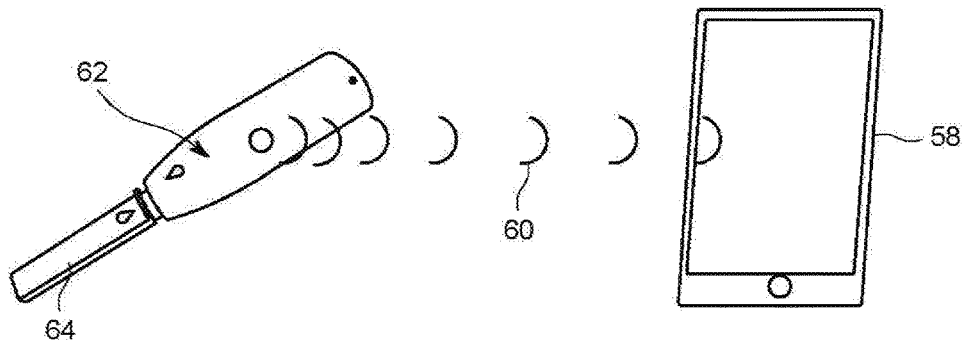
FIG. 5 is a schematic representation of the test cartridge of FIG. 1, inserted into an electronic reading device, where the reading device sends a wireless signal to a handheld computing device, according to an exemplary embodiment of the present invention.

Referring now to FIGS. 4 and 5, two incident light paths 48 emitted from two individual light-emitting diodes (LEDs)

50 can be aligned and collimated at the test line 32 and the control line 34. A test line photosensitive sensor 44 and a control line photosensitive sensor 54 may be located beside each LED 50 to receive the reflecting lights 46, 52 from the test line 32 and the control line 34, respectively. The electronic signals from the sensors 44, 54 can be transmitted to a microprocessor 56 for further data processing. In some embodiments, the electronic reading device 62, with the inserted test cartridge 64 may be configured to send a wireless signal 60, via a wireless protocol, such as Bluetooth, to a computing device 58, such as a tablet computer, smart phone or the like. The computing device 58 may be configured to provide output data, such as test results, quantitative analysis, or the like, to the user.

In some embodiments, as discussed in greater detail below, when the inserted test cartridge 64 is inserted into the electronic reading device 62, the performance of the test cartridge analysis can proceed without requiring the user to push any buttons. The computing device 58, once it receives the data via the wireless signal 60 from the microprocessor 56, can include software to process the test data as desired. The software may further provide for traceability of test results by inputting user information such as user name, patient ID, or the like, and the test results may be saved on the computing device or on connected external storage.

Figure 6:
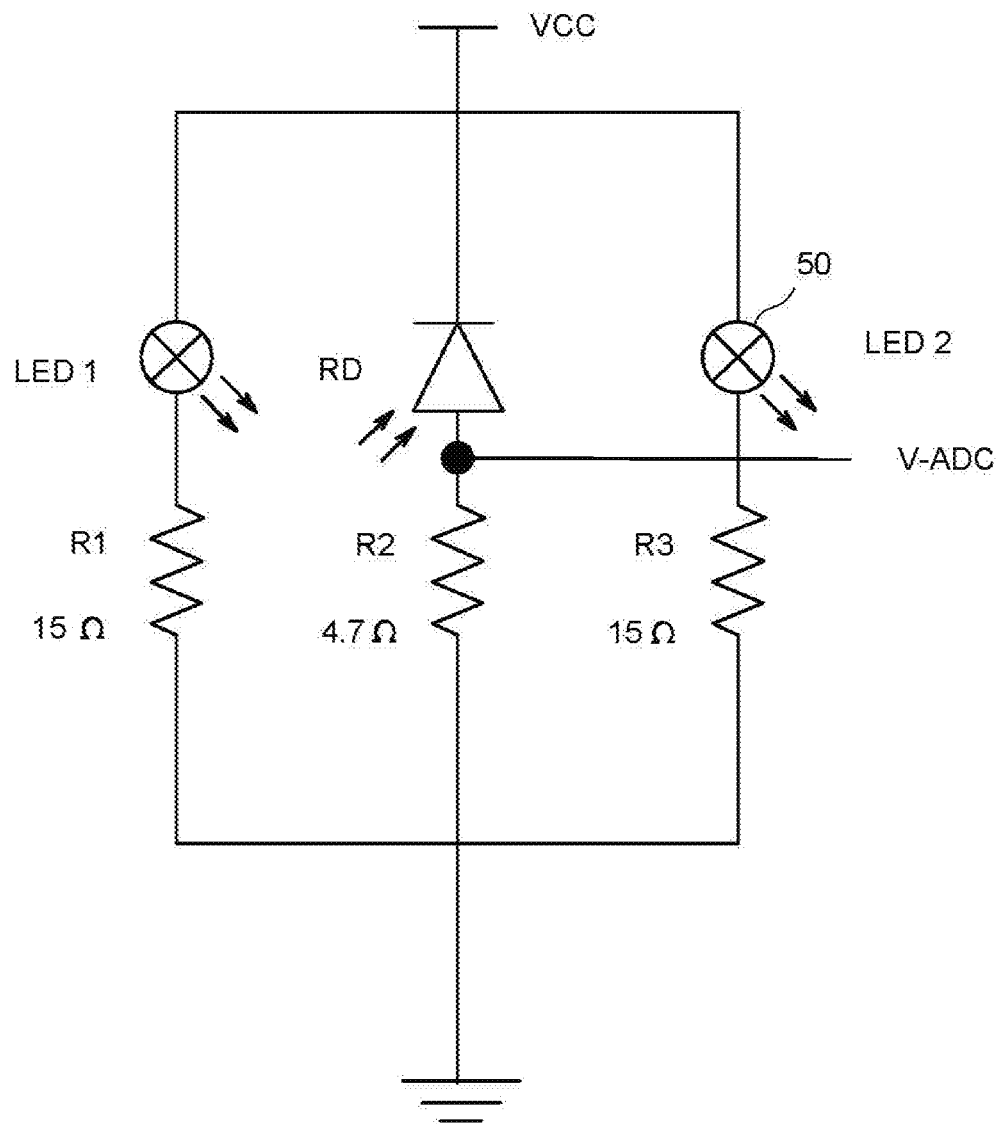
FIG. 6 is a circuit diagram illustrating an exemplary shunt regulator to provide a constant stabilized voltage to the lamps of the electronic reading device.
Figure 7:
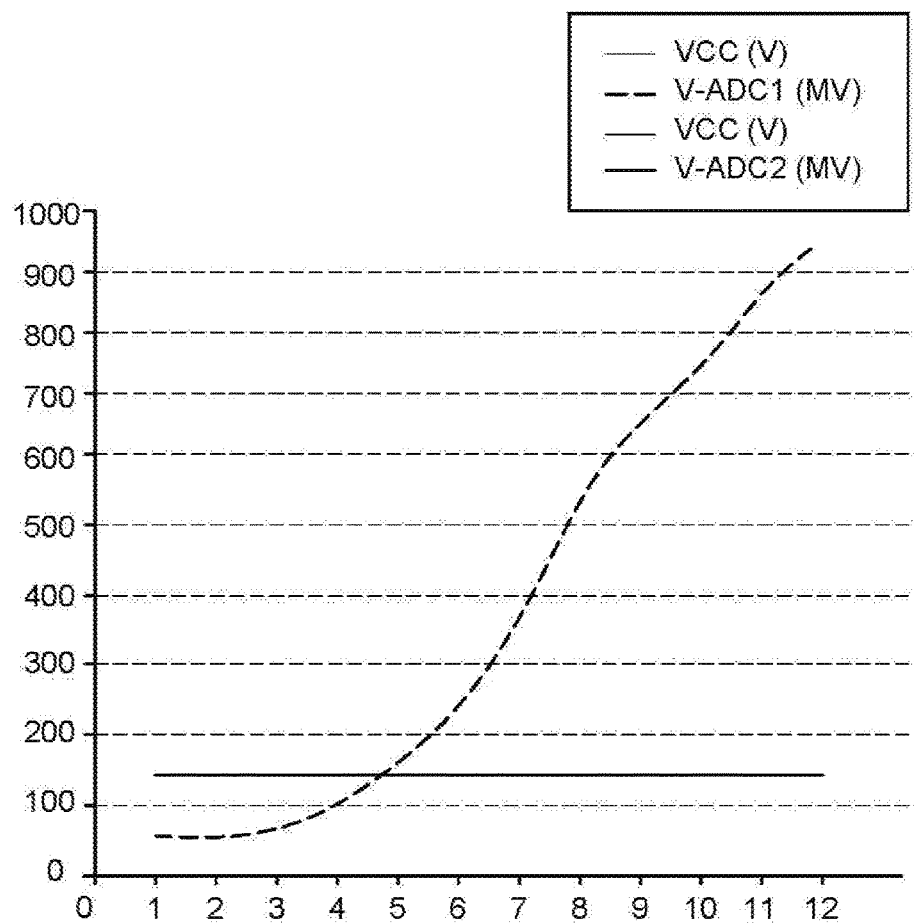
FIG. 7 is a graph showing how the shunt regulator of FIG. 6 provides a constant stabilized voltage.

Referring now to FIGS. 6 and 7, a shunt regulator circuit is shown in FIG. 6 that is capable of providing a constant stabilized voltage. LED1 and LED2 are surface mount LED lamps and RD indicates a photosensitive sensor. The graph of FIG. 7 is based on the Table 1 below, where V-ADC1 (MV) and VCC (MV) are represented on the graph, where V-ADC1 is the output voltage while VCC is the input voltage. As can be seen, fluctuations in input voltage with the shunt regulator circuit results in little if any change in voltage.

|  | Without shunt regulator | | With shunt regulator | |
| --- | --- | --- | --- | --- |
| No. | VCC (V) | V-ADC (MV) | VCC (V) | V-ADC2 (MV) |
| 1 | 2.48 | 59 | 2.8 | 156 |
| 2 | 2.56 | 62 | 2.8 | 1.55 |
| 3 | 2.64 | 70 | 2.8 | 155 |
| 4 | 2.74 | 107 | 2.8 | 154 |
| 5 | 2.82 | 176 | 2.8 | 154 |
| 6 | 2.91 | 250 | 2.8 | 156 |
| 7 | 3.07 | 390 | 2.8 | 155 |
| 8 | 3.25 | 547 | 2.8 | 154 |
| 9 | 3.37 | 678 | 2.8 | 156 |
| 10 | 3.46 | 750 | 2.8 | 156 |
| 11 | 3.55 | 856 | 2.8 | 155 |
| 12 | 3.66 | 917 | 2.8 | 155 |

In the present invention, in order to increase the repeatability and precision of the digital test result, a constant stabilized voltage to the LED 50 is incorporated. Some digital devices, such as those in U.S. Pat. Nos. 8,828,329; 9,453,850; 9,588,113; and 7,220,597 and U.S. Patent Publication No. 2013/0040401, adapt the disposable button cell battery to supply the LED. However, the low capacity of cell batteries cannot provide stabilized voltage during the testing because voltage discharges or battery voltage attenuates from time to time. Therefore, there can be no guarantee the device will work properly due to the lack of stabilized power control.

Figure 8:
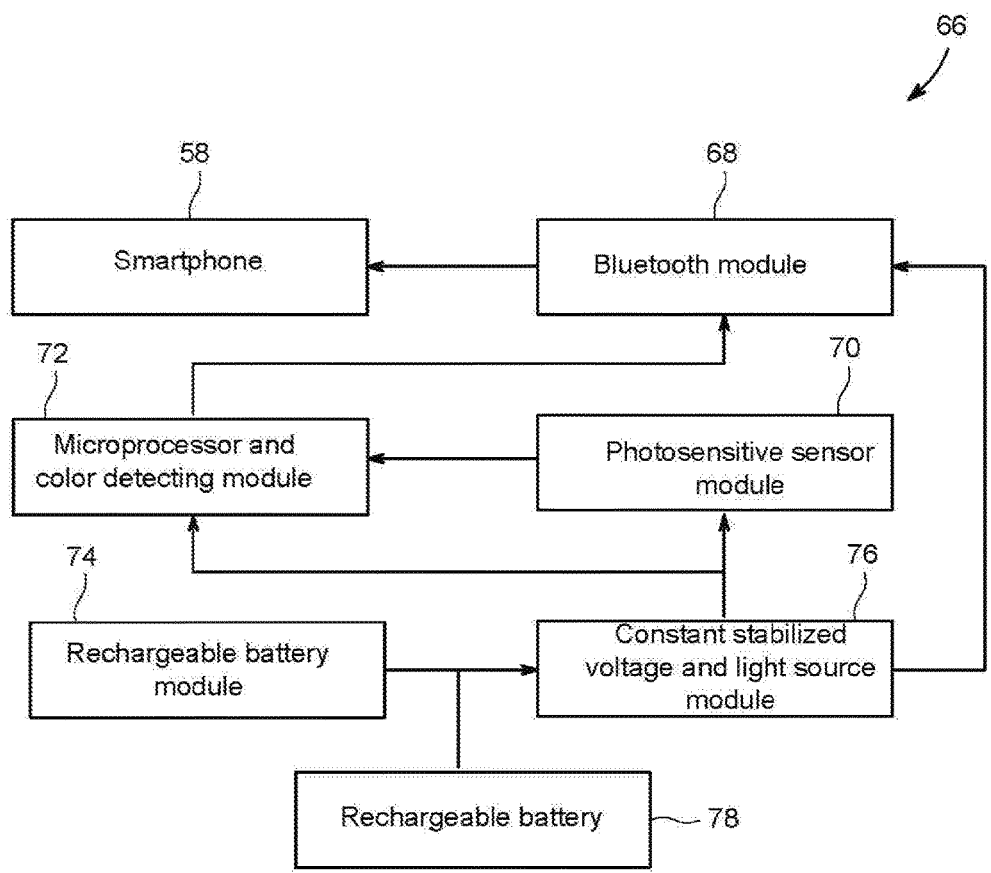
FIG. 8 is a schematic representation of the components of the electronic reading device.

Referring to FIG. 8, in order to improve this issue, a 3.6V, 40 mA rechargeable battery 78, as part of rechargeable battery module 74, coupled with a constant stabilized voltage and light source module 76, which can incorporate a shunt regulator, such as TL431S, from Texas Instruments, can provide constant stabilized voltage at 2.8V, which is optimal for the working voltage range of 2.7-2.8 V of the surface mount LEDs. Once the voltage is below 2.8V, a message can be provided to the user on their computing device 58 to remind the user to recharge the electronic device by using an appropriate charging cord. The 3.6V battery also provides the power for the wireless transmission, such as a Bluetooth module 68.

In order to improve the accuracy of the test result, the electronic reading device 62 can include a color recognition sensor detecting module 72 that receives signals from the photosensitive sensors 44, 54 (referred generally as photosensitive sensor module 70 in FIG. 8) and RGB individual vectors and then outputs a signal to the microprocessor 56 in which they are compared with a build-in database. The final output signals from the microprocessor 56 can be transmitted by Bluetooth module 68 to the computing device 58 for display to the user.

Figure 9:
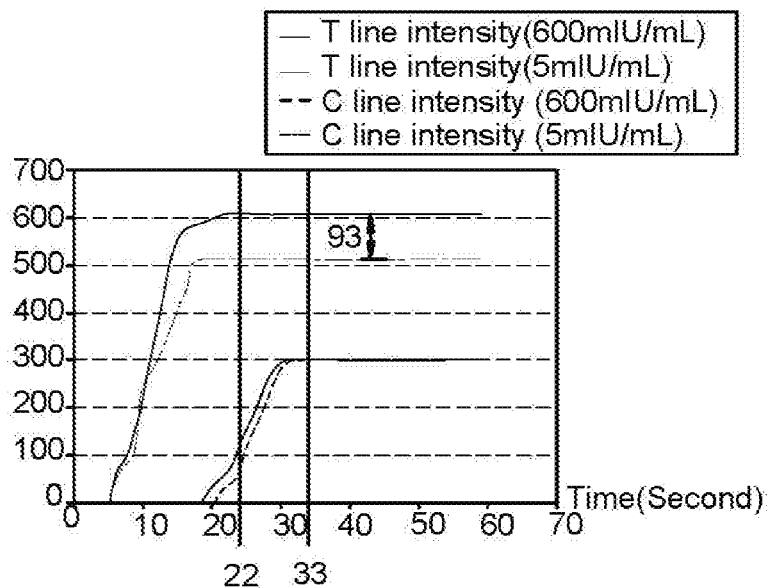
FIG. 9 is a graph showing two concentrations of sample run on the driven flow test cartridge of FIG. 1 and read on the electronic reading device.

Referring now to FIG. 9, the test performance of the cartridge and electronic reading device are described. In this analysis, hCG strips with 25 mIU/mL cutoff value are used for running a test with the following steps. First, one strip is assembled into the cartridge. Next, one drop (about 45 µL) of 5 or 600 mIU/mL standard control (as confirmed by GC/MS) is added into the sampling well 22. The cap is immediately placed on the cartridge. The cartridge is then placed in to the electronic reading device 62. The intensities of the test line and the control lines are measured over time and the values are expressed in FIG. 9.

Through the electronic reading device, the intensities of the test line and the control line is measured every second. From the two test line intensities of FIG. 9, the driven flow effect to drive specific molecular binding with antigen on the membrane was completed after 22 seconds and were stabilized through one minute with very subtle variation. From the two control line intensities of FIG. 9, they developed around 15 seconds later than the test line because of the lagging migration time behind the test line. The intensities of the control line become stable after 33 seconds and last until one minute.

The feasibility of quantitative analysis is observed by the intensity gap of the test lines between the 5 mIU/mL and the 600 mIU/mL concentrations. A significant intensity gap was noted of around 93 based on electron-magnified scale which is more reliable and precise than vision interpretation. This makes the test result become quantitative based on the intake human chorionic gonadotropin detected concentration versus electron-magnified signals.

An accuracy, repeatability and precision validation of the digital driven flow cartridge of the present invention was conducted. In this validation, two sampling methods, "stream fluid" and "dropped fluid" are involved with negative, 5 mIU/mL and 600 mIU/mL control specimens, respectively. Each 10 strips from three different lots of hCG strips were assembled in cartridges. Each test was run by experienced technicians and the results were recorded with "negative", "positive" or "invalid" and an electron-magnified signal was observed at 1 minute.

In the "stream fluid" method, 20 mL of specimen is poured gradually at 45 degrees on the opening end of the cartridge, as shown in FIG. 1. After finishing the sampling, the cartridge is inserted into the electronic reading device 62 and the testing is initiated.

In the "dropped fluid" method, one droplet (about 45 µL) of specimen is dropped on the sampling well 22 of the cartridge of FIG. 1. After finishing the sampling, the cartridge is inserted into the electronic device 62 and the testing in initiated.

The table below summaries the validation test results.

| Method | Strip Lot | Signal intensity of neg. specimen | Test result on neg. specimen | Signal intensity of 5 mIU/mL specimen | Test result on 5 mIU/mL specimen | Signal intensity of 600 mIU/mL specimen | Test result of 600 mIU/mL specimen |
|---|---|---|---|---|---|---|---|
| Stream | A | 0-10 | (−) 10/100% | 510-515 | (+) 10/100% | 602-607 | (+) 10/100% |
|  | B | 0-11 | (−) 10/100% | 510-515 | (+) 10/100% | 602-607 | (+) 10/100% |
|  | C | 0-9 | (−) 10/100% | 510-515 | (+) 10/100% | 602-607 | (+) 10/100% |
| Pipette | A | 0-9 | (−) 10/100% | 510-515 | (+) 10/100% | 602-607 | (+) 10/100% |
|  | B | 0-9 | (−) 10/100% | 510-515 | (+) 10/100% | 602-607 | (+) 10/100% |
|  | C | 0-11 | (−) 10/100% | 510-515 | (+) 10/100% | 602-607 | (+) 10/100% |

From all 180 tests results above, they show the digital driven flow cartridge complies 100% in accuracy, repeatability and precision under three hCG concentration levels of negative, 5 mIU/mL and 600 mIU/mL.

Figure 10:
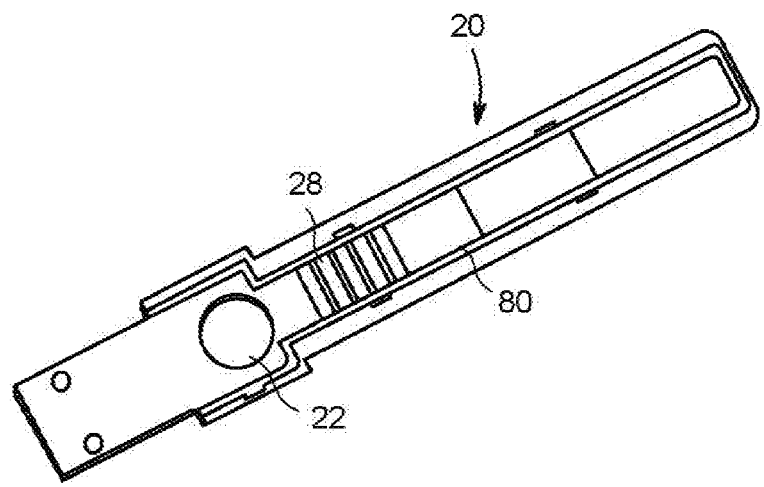
FIG. 10 is a plan view of a top component of the test cartridge of FIG. 1.
Figures 13A, 13B:
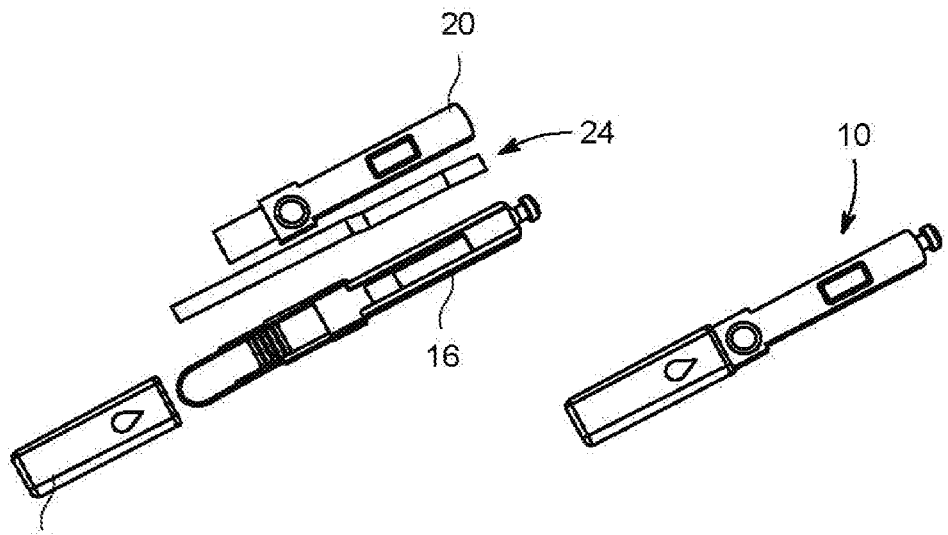
FIG. 13A is an exploded view of the test cartridge of FIG. 1.
FIG. 13B is a plan view of the test cartridge of FIG. 1 fully assembled.
Figures 14A, 14B:
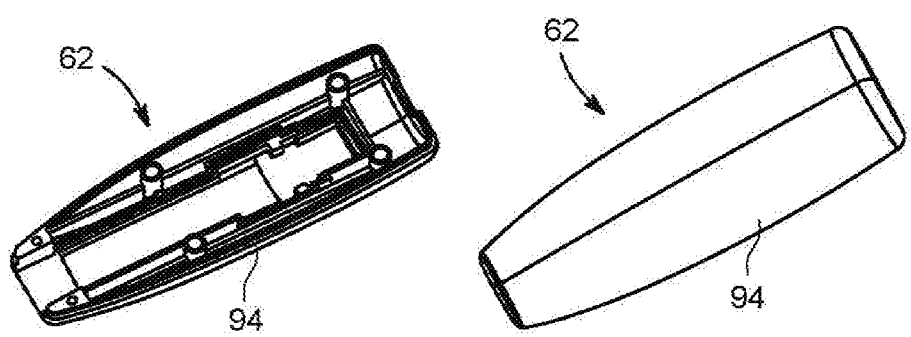
FIG. 14A is a top view of a base housing of an electronic reading device.
FIG. 14B is a bottom view of the base housing of the electronic reading device.

Referring now to FIGS. 10 through 13B, the components of the test cartridge 10 are shown in greater detail. FIG. 10 shows the top component 20 with a single reading window 80, one sampling well 22 and five compression bars 28. FIG. 11 shows the base component 16, illustrating the refracting pad for sampling 86, reservoir 42, compression cushion 84 which acts opposite the compression bars 28 of the top component 20 and a trigger head 82. The trigger head 82, as discussed below, can turn on the light source and start the testing when the cartridge is inserted into the electronic reading device. FIGS. 12A and 12B show the cap 90 that fits over the end of the cartridge and covers the exposed sample pad of the testing strip. The cap 90 can include a compression ramp 88 to modulate the pressure of the compression bars 28 to the conjugate pad 18. The cartridge 10 may be assembled as shown in FIGS. 13A and 13B, inclusive of the test strip 24.

Referring now to FIGS. 14 through 22, the components of the electronic reading device 62 are shown in greater detail. In FIGS. 14A and 14B, the bottom housing 94 is shown. The top housing 96 of FIGS. 15A and 15B may onto the bottom housing 94. A power light hole 98 may be formed in the top housing 96 to allow a user to see a lamp indicating that the electronic reading device 62 is powered on. FIG. 16 illustrates a light mask 108 having an opening 100 for a light switch and an LED light window 102. The light mask 108 can keep the light emitting and reflecting in a dark background. FIG. 17 shows the trigger head receiver 104. The trigger head 82 of the cartridge 10 may fit into an opening 106 of the trigger head receiver 104 to turn on the electronic reading device and begin the testing procedure.

Figure 18:
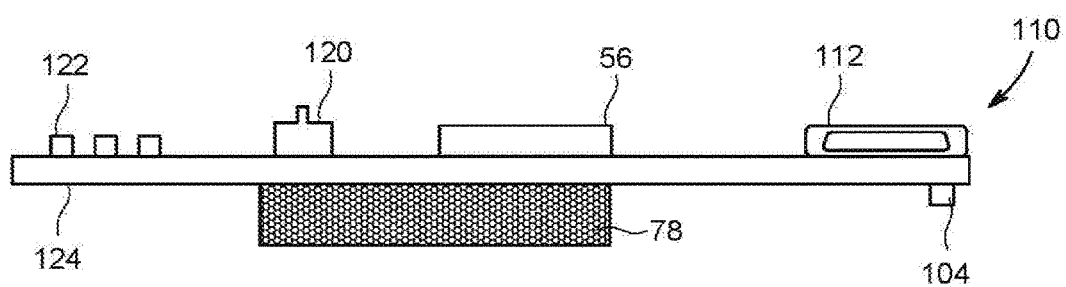
FIG. 18 is a side view of a printed circuit board used in the electronic reading device.

FIG. 18 shows a printed circuit board 110 that controls the electronic reading device 62. The printed circuit board can include three LED lights 122, a light switch 120, a microprocessor 56, a port 112, such as a micro USB port, a power light 104 and a rechargeable battery 78.

Figure 19:
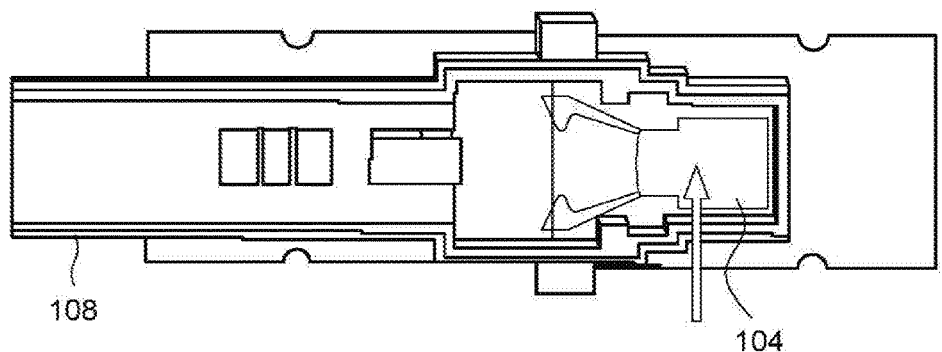
FIG. 19 is a top view of the trigger head receiver of FIG. 17 assembled with the light mask of FIG. 16.
Figure 20:
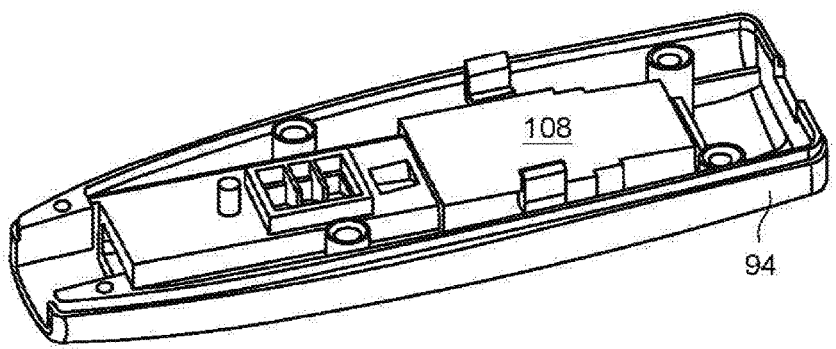
FIG. 20 is a perspective view of the assembly of FIG. 19 assembled into the base housing of FIGS. 14A and 14B.
Figure 21:
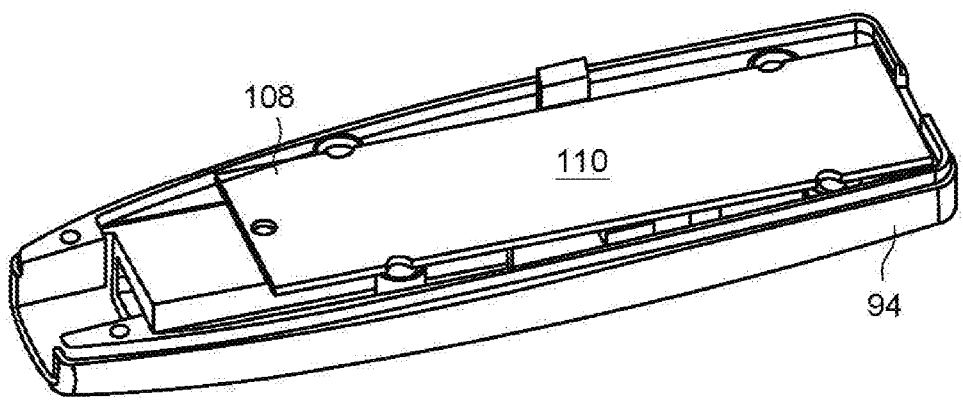
FIG. 21 is a perspective view of the assembly of FIG. 20 assembled with the printed circuit board of FIG. 18.
Figure 22:
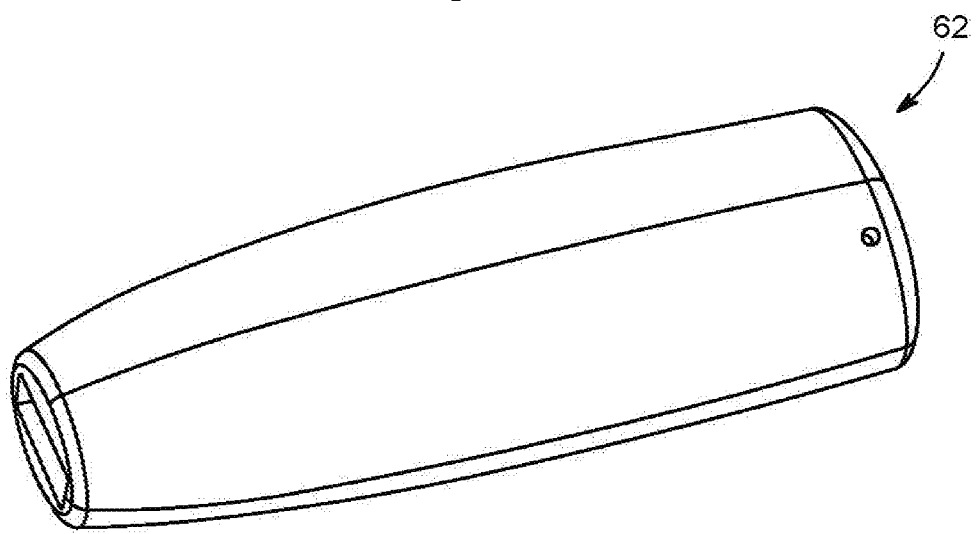
FIG. 22 is a perspective view of the assembly of FIG. 21 assembled with the top housing of FIGS. 15A and 15B.

As shown in FIG. 19, to assemble the electronic reading device 62, a user can place the trigger head receiver 104 into the light mask 108. Next, as shown in FIG. 20, the assembly of FIG. 19 can be placed into the base housing 94. The printed circuit board 110 may then be placed on the top of the light mask 108 as shown in FIG. 21, and the top housing 96 may then be placed on the bottom housing 94 to create the electronic reading device 62.

Figure 23:
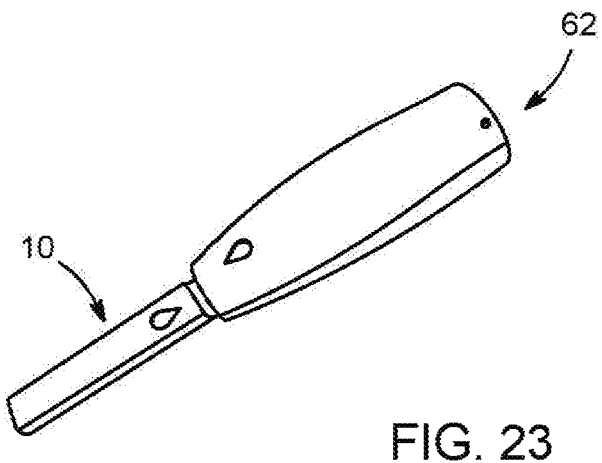
FIG. 23 is a perspective view of the test cartridge of FIG. 1 assembled with the electronic reading device of FIG. 22.

FIG. 23 shows the electronic reading device 62 in use with a cartridge 10 inserted therein.

The dual sampling method in a single cartridge, as provided by embodiments of the present invention, provides at least two choices for sampling for point-of-care (POC) and over-the-counter (OTC) testing. The cartridge, being made with specially designed compression bars and a refracting pad that converts a stream force into a driven flow force by refracting/pressing/squeezing/leading the stream to the reaction area that elutes and releases nanoparticle conjugate completely from the conjugate pad to the reaction zone. The testing time with the cartridge of the present invention is between about 30 seconds to about 1 minute, which is about 10 times faster than traditional lateral flow devices, which typically take from about 5 minutes to about 10 minutes.

The digital device of the present invention includes the progressive compression driven flow cartridge integrated with an electronic reading device which makes the reading of the result fast, easy and accurate. The digital texture format in this device provides quantitative concentration of analytes, for example, the concentration of intake human chorionic gonadotropin, which may be detected from about 5 to about 600 mIU/mL. The device of the present invention significantly increases the accuracy in interpreting the test result versus vision interpretation.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Claim elements and steps herein may have been numbered and/or lettered solely as an aid in readability and understanding. Any such numbering and lettering in itself is not intended to and should not be taken to indicate the ordering of elements and/or steps in the claims.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. A device for testing a liquid sample for the concentration of at least one analyte, comprising:
    a test cartridge comprising:
        a base component supporting a test strip;
        a top component fitting onto the base component, sandwiching the test strip with the base component;
        a plurality of compression bars on the top component, the compression bars aligning with a conjugate pad of the test strip when the test strip is positioned in the test cartridge;
        a refracting pad formed from an end of the base component for converting a fluid stream to a driven flow source, the refracting pad supporting a sample pad of the test strip when the test strip is positioned in the test cartridge, wherein the top component terminates prior to the refracting pad, permitting the fluid stream to be received on the sample pad; and
        a reservoir formed in the base component under the sample pad, the reservoir configured to contain excess fluid from the fluid stream directed at the sample pad.

2. The device of claim 1, wherein the test cartridge further comprises a sample well formed as an opening in the top component for placement of a sample on the sample pad.

3. The device of claim 1, wherein the test cartridge further comprises a reading window formed as an opening in the top component, the reading window providing visual access to a test line and a control line of the test strip when the test strip is disposed in the test cartridge.

4. The device of claim 1, wherein the test cartridge further comprises a cushion on the base component, the cushion aligning with the compression bars when the top component is assembled with the base component.

5. The device of claim 1, wherein the test cartridge includes a cap fitting over an end of the test cartridge having the refracting pad.

6. The device of claim 5, wherein the cap includes an internal ramp configured to modulate pressure from the compression bars onto the conjugate pad of the test strip.

7. The device of claim 1, wherein the test cartridge further comprises a trigger head at an end opposite the refracting pad, the trigger head configured to activate an electronic reading device when the test cartridge is inserted therein.

8. The device of claim 1, further comprising:
    an electronic reading device comprising:
        first and second light emitting diodes configured to deliver light to a test line and a control line of the test strip when the test cartridge is inserted into the electronic reading device;
        first and second photosensitive sensors for receiving a reflected light from each of the test line and the control line of the test strip; and
        a microprocessor for receiving signals from the first and second photosensitive sensors.

9. The device of claim 8, wherein the electronic reading device further comprises a wireless module for sending data from the microprocessor to an electronic device.

10. The device of claim 8, wherein the electronic reading device further comprises a shunt regulator for providing a constant power supply from a rechargeable battery.

11. The device of claim 8, wherein the electronic reading device further comprises a trigger head receiver, receiving a trigger head of the test cartridge to activate reading of the test cartridge.

12. The device of claim 8, wherein the electronic reading device further comprises a light mask for controlling the emission of light from the light emitting diodes.

13. The device of claim 8, wherein the electronic reading device further comprises a port for charging a rechargeable battery.

14. A system for testing a liquid sample for the concentration of at least one analyte, comprising:
    a test strip comprising:
        a sample pad for receiving a sample;
        a conjugate pad containing nanoparticle conjugate;
        a test line for indicating a test result; and
        a control line for indicating the test result;
    a test cartridge comprising:
        a base component supporting the test strip;
        a top component fitting onto the base component, sandwiching the test strip with the base component;
        a plurality of compression bars on the top component, the compression bars aligning with the conjugate pad of the test strip;
        a refracting pad formed from a first end of the base component for converting a fluid stream to a driven flow source, the refracting pad supporting the sample pad of the test strip, wherein the top component terminates prior to the refracting pad, permitting the fluid stream to be received on the sample pad;
        a trigger head disposed on a second opposite end of the base component; and
        a reservoir formed in the base component under the sample pad, the reservoir configured to contain excess fluid from the fluid stream directed at the sample pad; and
    an electronic reading device comprising:
        first and second light emitting diodes configured to deliver light to a test line and a control line of the test strip when the test cartridge is inserted into the electronic reading device;
        first and second photosensitive sensors for receiving a reflected light from each of the test line and the control line of the test strip;
        a microprocessor for receiving a signal from the first and second photosensitive sensors; and
        a trigger head receiver, receiving a trigger head of the test cartridge to activate reading of the test cartridge.

15. The system of claim 14, wherein the test cartridge further comprises a sample well formed as an opening in the top component for placement of a sample on the sample pad.

16. The system of claim 14, wherein the test cartridge further comprises a cushion on the base component, the cushion aligning with the compression bars when the top component is assembled with the base component.

17. The system of claim 14, wherein the test cartridge includes a cap fitting over an end of the test cartridge having the refracting pad, wherein the cap includes an internal ramp configured to modulate pressure from the compression bars onto the conjugate pad of the test strip.

18. The system of claim 14, wherein the electronic reading device further comprises a wireless module for sending data from the microprocessor to an electronic device.

19. The device of claim 14, wherein the electronic reading device further comprises a shunt regulator for providing a constant power supply from a rechargeable battery.

20. A system for testing a liquid sample for the concentration of at least one analyte, comprising:
- a test strip comprising:
  - a sample pad for receiving a sample;
  - a conjugate pad containing nanoparticle conjugate;
  - a test line for indicating a test result; and
  - a control line for indicating the test result;
- a test cartridge comprising:
  - a base component supporting the test strip;
  - a top component fitting onto the base component, sandwiching the test strip with the base component;
  - a plurality of compression bars on the top component, the compression bars aligning with the conjugate pad of the test strip;
  - a cushion on the bottom component, the cushion aligning with the plurality of compression bars to sandwich the conjugate pad of the test strip there between;
  - a refracting pad formed from a first end of the base component for converting a fluid stream to a driven flow source, the refracting pad supporting the sample pad of the test strip, wherein the top component terminates prior to the refracting pad, permitting the fluid stream to be received on the sample pad; and
  - a reservoir formed in the base component under the sample pad, the reservoir configured to contain excess fluid from the fluid stream directed at the sample pad; and
- an electronic reading device comprising:
  - first and second light emitting diodes configured to deliver light to a test line and a control line of the test strip when the test cartridge is inserted into the electronic reading device;
  - first and second photosensitive sensors for receiving a reflected light from each of the test line and the control line of the test strip;
  - a microprocessor for receiving a signal from the first and second photosensitive sensors; and
    - a shunt regulator for providing a constant power supply from a rechargeable battery.

\* \* \* \* \*